United States Patent [19]

Suggitt et al.

[11] 4,042,490
[45] Aug. 16, 1977

[54] HYDROCARBON UPGRADING PROCESS

[75] Inventors: Robert M. Suggitt, Wappingers Falls; Walter C. Gates, Jr., Newburg, both of N.Y.

[73] Assignee: Texaco Inc., New York, N.Y.

[21] Appl. No.: 428,638

[22] Filed: Dec. 26, 1973

[51] Int. Cl.$^2$ .................. C10G 23/02; C10G 23/04
[52] U.S. Cl. .................... 208/264; 252/465; 252/466 J; 252/466 PT; 252/473; 252/474; 260/566 A; 260/583 M; 260/632 CB; 260/676 R
[58] Field of Search ............... 208/143, 264; 260/676 R, 683.9, 667, 639 B

[56] References Cited

U.S. PATENT DOCUMENTS

| 2,779,711 | 1/1957 | Goretta | 208/143 |
|---|---|---|---|
| 3,268,608 | 8/1966 | DeRosset | 260/683.9 |
| 3,322,843 | 5/1967 | Frandolig et al. | 260/676 R |
| 3,524,891 | 8/1970 | Cahn | 260/639 B |
| 3,580,837 | 5/1971 | Pollitzer | 208/143 |
| 3,694,703 | 3/1972 | Rausch | 260/667 |
| 3,730,877 | 5/1973 | Quik et al. | 208/143 |
| 3,836,453 | 9/1974 | Kovach et al. | 208/143 |
| 3,851,001 | 11/1974 | Suggitt | 260/683.9 |
| 3,859,370 | 1/1975 | Carter et al. | 260/683.9 |

Primary Examiner—Herbert Levine
Attorney, Agent, or Firm—Thomas H. Whaley; Carl G. Ries; George J. Darsa

[57] ABSTRACT

A process for converting mixtures of $C_6$ to $C_{30}$ n-paraffin and n-paraffin by-products to substantially pure n-paraffin which comprises catalytically hydrogenating the mixture at a temperature of from about 600° to 750° F. in the presence of a Group VIII metal on alumina catalyst where the catalyst contains from about 0.05 to 2.0 weight percent of an alkali metal oxide or alkaline earth metal oxide or thallous oxide. The catalyst can additionally contain a Group VIB or VIIB metal.

21 Claims, No Drawings

HYDROCARBON UPGRADING PROCESS

This invention relates to a process for converting mixtures containing n-paraffins to substantially pure n-paraffins. In particular this invention relates to a process for converting mixtures of $C_6$ to $C_{30}$ n-paraffins and $C_6$ to $C_{30}$ by-products to substantially pure $C_6$ to $C_{30}$ n-paraffins by catalytic hydrogenation.

Normal paraffin hydrocarbons having from 6 to 30 carbon atoms represent valuable feedstock materials which can be converted to highly desirable products including amines by nitration and hydrogenation or to oximes by photonitrosation or to secondary alcohols by oxidation. In the illustrative processes described above, from about 5 to 50 weight percent of the normal paraffin undergoes conversion which results in the formation of a crude product mixture containing not only the desired material and unconverted paraffin but additionally substantial amounts of oxygenated paraffin by-products which can in some instances be produced in equal quantities with the sought after product. The desired product, for example, the amine or oxime or secondary alcohol is separated and recovered from the crude reaction product leaving a raffinate composed of a mixture of n-paraffin and oxygenated n-paraffin. While the raffinate may be recycled for further conversion to the preselected product, the presence of the oxygenated compounds present innumerable problems including the substantial buildup of undesired by-products and the further conversion of the oxygenated hydrocarbons to multifunctional materials. The formation and buildup of substantial amounts of byproducts in turn seriously reduces the attractiveness and selectively of the process which ultimately leads to a highly unsatisfactory and cost prohibitive operation.

Heretofore, the n-paraffins contained in the mixture have been purified employing various procedures including the use of molecular sieve selective adsorbents to provide streams suitable for recycle substantially free of contaminants. However, this procedure is objectionable in that it removes substantial amounts of paraffin by-products, which by-products must be ultimately disposed of. This operation is particularly costly where by-product formation approximates the amount of desired product originally formed. Other techniques involved upgrading the mixture by hydrogenating crude normal paraffin mixtures containing oxygenated paraffins at temperatures of from about 450° to 600° F. in the presence of previously disclosed hydrogenation catalysts. However, even at this temperature range some hydrocracking to light paraffins and hydrogenolysis to methane occurred leading to losses in recoverable recycle material. Further, temperatures in excess of 600° F. were to be avoided as the same caused excessive undesirable isomerization, hydrocracking, hydrogenolysis and coking of the hydrocarbons to, for example, isoparaffins and methane. While hydrogenation of the crude mixture at 450° to 600° F. is not particularly effective inasmuch as some hydrocracking and isomerization occurs which reduces the amount of valuable feedstock which can be recycled, the oxygenated by-products are only partially hydrogenated such that a considerable amount of incompletely converted by-products are recycled.

It is therefore an object of this invention to provide a process which provides substantially pure n-paraffins from mixtures of n-paraffin and oxygenated paraffin hydrocarbons in high yields.

Another object of this invention is to provide a process for converting a mixture of n-paraffin and oxygenated paraffin to substantially pure n-paraffin.

Yet another object of this invention is to provide a process wherein mixtures of n-paraffins and oxygenated paraffin hydrocarbons are continuously converted to pure n-paraffin compositions.

Other objects and advantages will become apparent from a reading of the following detailed description and examples.

SUMMARY OF THE INVENTION

Broadly this invention contemplates a process for converting a mixture of n-paraffin and n-paraffin by-product s, that is, oxygenated paraffin, to substantially pure n-paraffin which comprises catalytically hydrogenating the mixture at a temperature of from about 600° to 750° F., preferably from 610° to 700° F., in the presence of a catalyst composed of alumina, a Group VIII metal and from about 0.05 to 2.0 weight percent of an alkali metal oxide, alkaline earth metal oxide or thallous oxide. The catalyst can also contain as a component thereof an oxide of a member from Group VIB or a member from Group VIIB.

The catalyst employed in our process is one which comprises a member of Group VIII of the Periodic Table, alumina and an alkali metal oxide or alkaline earth metal oxide or thallous oxide. Exemplary of the Group VIII metals are platinum, palladium, rhodium and ruthenium. Nickel and cobalt are also contemplated preferably in combination with a Group VIB metal oxide such as molybdenum oxide or tungsten oxide. A Group VIIB member such as rhenium present as the metal can also be used in combination with the Group VIII metal. Aluminas in various forms may be used as a component of the catalyst and particularly those aluminas having replaceable surface hydroxyl groups and surface areas of from 50 to 400 square meters per gram using the BET method. Included within our definition of alumina we mention, for example, eta-alumina, gamma-alumina, silica stabilized aluminas, i.e. aluminas containing up to approximately 5 weight percent $SiO_2$, thoria-alumina, zirconia-alumina, titania-alumina and chromia-alumina. The Group VIII metal is present in amounts ranging from about 0.1 to 5.0 weight percent, preferably from about 0.1 to 2.0 weight percent, for the noble metals and from 1 to 5 percent for nickel and/or cobalt, based on the composite catalyst. The Group VIB metal oxide component when present ranges from about 5 to 20 weight percent of the composite catalyst. The Group VIIB metal can be present in an amount of from about 0.1 to 2.0 weight percent.

The catalyst described above to be selective in converting the mixture of n-paraffin and oxygenated paraffin to substantially pure n-paraffin at a temperature of from about 600° to 750° F. requires as a component thereof from about 0.05 to 2.0 weight percent of an alkali metal oxide, alkaline earth metal oxide or thalous oxide or mixtures thereof. Illustrative of the alkali metals contemplated we mention lithium, sodium, potassium, rubidium and cesium and as the alkaline earth metals calcium, stontium and barium. The presence of the additional component moderates the activity of the Group VIII metal on alumina catalyst which in the absence thereof and at hydrogenation temperatures of from about 600° to 750° F. otherwise causes substantial isomerization and hydrocracking of the mixture to isoparaffins and light paraffins. The presence of the minor amount of alkali metal oxide, alkaline earth metal oxide or thallous oxide and mixtures or combinations thereof on the catalyst deters isomerization and hydrocracking of the mixture including the n-paraffin and by-products and thereby selectively converts the by-products to valuable n-paraffin recycle feedstock.

The catalyst described above can be prepared by introducing the Group VIII metal, and when desired the Group VIB or VIIB member, to the alumina by impregnating with an aqueous solution of a soluble salt of the metal followed by drying and calcination at a temperature of from 600° to 1200° F. for several hours. The alkali metal oxide, alkaline earth metal oxide or thallous oxide can likewise be introduced to the alumina by impregnating with a soluble salt, such as the nitrate or acetate, either simultaneously with or subsequent to the introduction of the Group VIII metal followed by drying and calcination at 600° to 1200° F.

The alumina component of the catalyst complements the hydrogenating activity of the Group VIII metal and moderator by promoting the dehydration of alcohols or glycols present to the corresponding olefin which are in turn hydrogenated to n-paraffin. This property of the catalyst is particularly beneficial not only at the operative hydrogenation temperature range of from 600° to 750° F., but the dual functional aspect of the catalyst is particularly advantageous in converting any olefinic material formed at the elevated temperatures and partially converted to n-paraffin to be essentially converted to n-paraffin by an additional and subsequent hydrogenation undertaken at about 450° to 650° F.

In a further embodiment, the mixture of $C_6$ to $C_{30}$ n-paraffin and oxygenated paraffin is initially hydrogenated at a temperature of from about 350° to 500° F., preferably from 400° to 450° F., and prior to the hydrogenation at 600° to 750° F. described above. Initial hydrogenation is particularly desirable when the mixture contains such oxygenated components as, for example, nitrites or nitrates which are thermally unstable at temperatures of 600° F. and higher. Such illustrative thermally unstable materials when introduced to reactor preheaters operated to raise the temperature of the mixture to about 600° to 750° F. prior to introduction of the mixture into the hydrogenation reaction, thermally decompose and form resinous deposits in the preheater. By initially hydrogenating the mixture at 350° to 500° F., the thermally unstable materials are converted to more stable forms which can thereafter be successfully heated to temperatures of 600° F. and higher in reactor preheaters. The initial hydrogenation also serves as a guard chamber to protect the catalyst employed at the 600° to 750° F. hydrogenation to convert some oxygenates to non-volatile inorganic compounds such as when the mixture contains alkyl borate esters described below. Conventional hydrogenation catalysts can be employed in the initial hydrogenation as, for example, nickel, cobalt, platinum, palladium and rhodium. The catalysts can be supported on kieslguhr, silica, carbon or alumina as is known in the art. The catalyst described above and employed at the hydrogenation conditions of 600° to 750° F. can also be used.

In some instances it may be desirable to pass the recycle mixture through a bed of alumina, silica gel or activated carbon to act as guard case for the hydrogenation catalyst. Illustratively, a recycle mixture derived from the conversion of paraffins to secondary alcohols will contain minor amounts of boric acid and borate esters which adversely affect hydrogenation catalysts. Such materials can be effectively removed from the mixture prior to hydrogenation by, for example, passing the mixture at 400° to 500° F. through a bed of activated alumina.

As mentioned above, an additional and subsequent hydrogenation may also be desirable as, for example, when the liquid product hydrogenated at 600° to 750° F. is found to contain minor amounts of $C_6$ to $C_{30}$ olefins. Such an additional hydrogenation treatment can be conducted at from about 450° to 650° F. wherein the olefin is converted to n-paraffin employing catalysts of the type described in connection with the hydrogenation at 600° to 750° F.

In general, hydrogenation in each of the above plural temperature ranges is undertaken in the presence of hydrogen at pressures ranging from about 100 to 1500 p.s.i.g. for periods of from 0.2 to 5 hours. In continuous processing the mixture can be introduced into the hydrogenation zones at space velocities of from 0.2 to 10.0 volumes of liquid feed per volume of catalyst per hour (v./v./hr.)

The mixtures hydrogenated according to the instant invention and composed of n-paraffins having from 6 to 30 carbon atoms and n-paraffin by-products, that is, oxygenated paraffins having from 6 to 30 carbon atoms can be derived from a plurality of sources. Typically, the mixture contemplated for hydrogenation in accordance with the instant invention is predominantly $C_6$ to $C_{30}$ n-paraffin containing from 0.5 to 30 weight percent oxygenated paraffins. Representative of the $C_6$ to $C_{30}$ oxygenated paraffins are alcohols, ketones and polyoxygenated materials such as acids, esters, glycols, lactams, ketoacids, and ketoalcohols. The mixture depending upon its source can also contain additional materials capable of being converted to normal paraffins in the presences of the catalyst described above and under the hydrogenation conditions recited. Among such materials are included $C_6$ to $C_{30}$ nitroparaffins, secondary amines, diamines, nitroalcohols, aminoalcohols, aminoketones, nitroketones, nitrates, nitrites, dinitro-paraffins, alkylchlorides and olefins.

Illustrative of the sources of the mixtures hydrogenated herein we mention the following. In the production of secondary alkyl primary amines from n-paraffins having from 6 to 30 carbon atoms, the amines are prepared by nitrating from about 5 to 50 weight percent of the paraffin to nitroparaffin employing as nitrating agent, for example, nitric acid, nitrogen dioxide or dinitrogen tetroxide at a temperature of from about 250° to 500° F. to form a crude nitrated product containing in addition to unconverted n-paraffin and nitroparaffin substantial quantities of oxygenaated by-products such as $C_6$ to $C_{30}$ ketones, alcohols, carboxylic acids, nitrites, nitrates and multifunctional materials such as dinitroparaffins, nitroalcohols, nitroketones and ketoalcohols. Thereafter the crude nitrated liquid product typically comprising from 50 to 94.5 weight percent unreacted n-paraffin, 5 to 35 weight percent nitroparaffin and 0.5 to 15 weight percent oxygenated by-products is introduced to a hydrogenation zone where the nitroparaffin is hydrogenated to the amine at average conversion temperatures ranging from about 100° to 450° F. in the presence of conventional and well known hydrogenation catalysts. A preferred catalyst is palladium on carbon. The crude liquid hydrogenated product comprises $C_6$ to $C_{30}$ n-paraffin secondary alkyl primary amine and oxygenated by-products such as acids, alcohols, ketones, ketoalcohols, aminoalcohols, aminoketones, nitrates and nitrites. Other by-products such as unreacted nitroparaffin, secondary amines and diamines can also be present. The primary amine is separated from the liquid hydrogenated product employing conventional recovery procedures such as step-wise fractionation or the amine may be converted and recovered as an amine salt by reaction of the crude liquid product with an inorganic acid followed by further treatment of the amine salt with alkali and thereafter recovering the primary amine by distillation. The unreacted nitroparaffin and oxygenated or other by-products of the nitration hydrogenation reactions in admixture with the paraffin, secondary amines and diamines separated from the primary amine represent a typical mixture contemplated by the instant invention which is hydrogenated to substantially pure n-paraffin.

The production of secondary alcohols from $C_6$ to $C_{30}$ n-paraffins also provides by-product streams composed of mixtures of n-paraffin and oxygenated paraffins which are according to the instant invention converted to substantially pure n-paraffin. The production of secondary alcohols from $C_6$ to $C_{30}$ paraffins is accomplished by contacting the paraffin in the liquid phase with an oxygen containing gas in the presence of boric acid at a temperature of from about 300° to 450° F. to convert from 5 to 50 weight percent of the paraffin to a mixture of alkyl borate esters, unreacted paraffin and degradation products including olefins and oxygenated products other than the borate esters. The mixture is first fractionated to separate an overhead fraction comprising unreacted n-paraffins, a portion of the by-products including such materials as olefins, ketones, some alcohols and traces of borate ester, and a bottoms fraction containing the borate ester and polyoxygenated by-products including ketoalcohols, acids, ketoacids and glycols. The bottoms are contacted with water at from 100° to 212° F. to hydrolyze the borate esters to secondary alcohols which bottoms separate into two phases comprising a top organic layer containing secondary alcohol and substantially all of the polyoxygenated products and a bottom layer comprised of aqueous boric acid, which layers are separated. The organic layer is fractionated to separate desired secondary alcohols as an overhead and a bottoms comprising polyoxygenated materials. The overhead recovered by the first fractionation comprised of unreacted n-paraffins, olefin and oxygenated products including alcohols and ketones represents a typical mixture contemplated for hydrogenation according to the instant invention. All or a portion of the final organic bottoms containing the polyoxygenated by-products can also be included into the mixture contemplated for hydrogenation herein.

Another process providing mixtures of n-paraffin and oxygenated paraffins, which according to the instant invention can be substantially converted to pure n-paraffins, involves the production of normal paraffinoximes having from 6 to 30 carbon atoms from normal paraffins. The oximes are prepared by photochemically reacting and converting from 5 to 50 weight percent of a $C_6$ to $C_{30}$ normal paraffin with a gaseous nitrosating agent, such as nitrosyl halides, nitrosyl sulfuric acid, nitrogen oxide and chlorine or nitrogen peroxide and chlorine at a temperature of from about 30° to 140° F. under the influence of light to produce normal paraffin oximes and up to about 5 weight percent oxygenated by-products primarily composed of ketones. Some alkylchlorides are also formed. The oxime is thereafter converted to the sulfate and uncoverted $C_6$ to $C_{30}$ paraffin, ketones and alkychlorides are extracted using a low boiling hydrocarbon such as cyclohexane, n-pentane, isoheptane or petroleum ether. Thereafter the low boiling hydrocarbon is separaated by distillation and the mixture of the n-paraffin, oxygenated paraffin, in this instance ketones, along with the alkylchlorides, can be converted to substantially pure n-paraffin according to he instant invention.

It will be appreciated that other known processes providing mixtures of n-paraffin and oxygenated paraffin by-products can be improved by applicants' catalytic hydrogenation and that the processes mentioned above are merely illustrative and are not intended to limit the instantly claimed invention.

In order to illustrate more fully the nature of our invention and manner of practicing the same, the following examples are presented. In these examples the best mode contemplated by us for carrying out our invention is set forth.

EXAMPLE I

The conversion of n-paraffins to secondary alkyl primary amines is undertaken by providing a fresh water-white $C_{10}$ to $C_{14}$ n-paraffin hydrocarbon composition having the following carbon chain length distribution on a weight percent basis: $C_{10}$ 11.1, $C_{11}$ 28.7, $C_{12}$ 32.2, $C_{13}$ 26.9, $C_{14}$ 1.1. To 10.7 weight percent of fresh normal paraffins there is mixed 89.3 weight percent of previously processed and upgraded recycle paraffins according to the instant invention.

A paraffin hydrocarbon charge at the rate of 940 pounds per hour is nitrated with 60 pounds per hour of nitrogen dioxide wherein nitration proceeds at 330° F. under a pressure of 4 p.s.i.g. Off-gases comprising paraffin, nitrogen dioxide, nitric oxide, nitrous oxide, nitrogen, carbon dioxide, carbon monoxide and wa er are withdrawn, the off-gases partially condensed, and condensed paraffin recycled. Nitric oxide in the overhead gas is oxidized to nitrogen dioxide, the oxidized gas cooled to condense nitrogen dioxide, and the liquefied nitrating agent recycled. Non-condensible gases including nitrogen, nitric oxide, nitrous oxide, carbon monoxide and carbon dioxide are vented.

The crude nitrated paraffin product, 977 pounds, comprising 80 weight percent n-paraffin, 14.7 weight percent nitroparaffin and 4.4 weight by-products including oxidized paraffin and polyfunctionals of which 0.6 weight percent are ketones, 1.2 weight percent are nitrites and 0.5 weight percent are nitra es is continuously caustic washed with about 70 pounds per hour of 10 percent aqueous sodium hydroxide in a line mixer at 200° F. and 50 p.s.i.g. The resulting aqueous layer is separated in a settler and removed. The organic layer is washed at 180° F. and 50 p.s.i.g. with 27 pounds per hour of water in a conventional countercurrent extraction tower. The washed nitrate product contains 129 pounds of nitrated paraffin and 833 pounds of n-paraffin and other materials that include 0.43 weight percent ketones, 0.95 weight percent nitrites and 0.41 weight percent nitrates.

The crude nitrated paraffin composition is introduced at an inlet temperature of 200° F. to a hydrogenation reactor containing a hydrogenation catalyst composed of one weight percent palladium on carbon at a liquid hourly space velocity of 2.0 volumes of liquid per volume of catalyst per hour. Hydrogenation is conduct ed under a hydrogen pressure of 560 p.s.i.g. and up to a maximum conversion temperature of 410° F. Folling hydrogenation, substantially all of the nitroparaffin is reduced to amine. Hydrogen, ammonia and some water are removed as gases and remaining water and ammonia are decanted from the recovered crude hydrogenation product at 110° F.

The crude hydrogenation product at a rate of 950 pounds per hour comprising 834 pounds of n-paraffins and miscellaneous by-products including 0.49 weight percent amines (secondary) and 0.52 weight percent ketones, 100 pounds of secondary alkyl primary amine, about 1 pound of unconverted nitroparaffins and 15 pounds of water and ammonia is contacted and saturated with 87 pounds per hour off carbon dioxide at 300 p.s.i.g. and 110° F. thereby forming an amine-carbon dioxide complex. The carbon dioxide saturated crude hydrogenation product is counter-currently contacted in a tower with 1,500 pounds per hour of a solvent mixture comprising 40 percent methanol and 60 percent water, the solvent mixture having been previously saturated with 50 pounds per hour of carbon dioxide at 300 p.s.i.g. and 110° F. Upon contacting of the carbon dioxide saturated crude hydrogenation product with the solvent mixture, the primary amine complex transfers from the predominantly paraffin stream to the solvent stream.

The amine depleted paraffin stream is subsequently reduced to atmospheric pressure in a flash drum whereupon carbon dioxide therein is removed overhead. The amine-enriched solvent stream is heated to a temperature of 150° F. and introduced to a flash tower maintained at atmospheric pressure where carbon dioxide, along with some methanol and water is removed overhead. The amine-rich liquid from the flash tower is passed through a fractionator where methanol, residual carbon dioxide and some water are emoved overhead. The bottom stream containing stream containing water and crude amines separates as two phases, namely a water phase containing some methanol and amines, and a crude amine phase containing some water.

110 pounds per hour of the crude amine phase are heated to 248° F. and flashed at 160 mm. Hg thereby removing as overhead substantially all of the residual methanol and water, along with some organic materials. After condensation, the organic matter in the overhead is separated from the aqueous layer and combined with the flashed amine phase. The flashed crude amine phase is thereafter vacuum-distilled at 20 mm. Hg and 200° F. to remove overhead residual methanol, water, paraffinic hydrocarbons and lighter than $C_{10}$ amines. Finally, the amine phase is vacuum distilled at 10 mm. Hg and 300° F. to produce 100 pounds per hour of finished amine containing 98.5 weight percent secondary alkyl primary amine.

The amber colored amine-depleted paraffin stream from the raffinate flash drum is combined with the predominantly paraffinic waste streams derived from vacuum distilling the crude amines to form a recycle stream comprising about 98 weight percent n-paraffin, 0.15 weight percent nitroparaffins and about 1.85 weight percent by-products. The mixed recycle stream is introduced into an initial hydrogenation zone at the rate of 840 pounds per hour and hydrogenated at 400° F. with 17 pounds per hour of hydrogen at 500 p.s.i.g. at a liquid hourly space velocity of 3.0 in the presence of a nickel-molybdenum on alumina catalyst. The product of the initial hydrogenation zone is introduced into a subsequent hydrogenation zone at the rate of 840 pounds per hour and hydrogenated at 660° F. with 16 pounds per hour of hydrogen at 500 p.s.i.g. at a liquid hourly space velocity of 1.5 in the presence of a 3 weight percent nickel oxide-12 weight percent molybdenum oxide — 0.6 weight percent barium oxide on alumina catalyst. After separating hydrogen, ammonia and water, the hydrogenated water-white product is essentially free of nitrated and oxygenated by-products and is recycled for introduction to the nitration reactor. The system for producing the amines continues to operate for long periods of time without interruption.

EXAMPLE II

An amine-depleted $C_{10}$ to $C_{14}$ paraffin stream composed of about 3 weight percent by-products including nitroparaffins, ketones, secondary amines, alcohols, nitrates, nitrites and polyfunctional derivatives of the n-paraffin similar to Example I was introduced into a hydrogenation reactor containing a nickel on kieselguhr hydrogenation catalyst at the rate of 3.3 pounds per hour and hydrogenated at 610° to 615° F. with 0.03 pounds per hour of hydrogen at about 600 p.s.i.g. Sampling of the off-gas shows it to contain 7 percent methane thereby demonstrating that substantial hydrocracking has occurred.

EXAMPLE III

A continuous process for converting n-paraffin to secondary alcohols is undertaken by introducing a $C_{10}$ to $C_{14}$ n-paraffin charge composed of 12.6 weight percent fresh n-paraffin and 87.4 weight percent recycle n-paraffin hydrogenated according to this invention.

815 pounds per hour of the paraffin charge is preheated to 350° F. and introduced to two continuous stirred tank reactors in series along with orthoboric acid, the acid added at the rate of 2.1 weight percent basis total paraffin charge to each reactor for a total of 4.2 weight percent boric acid basis the total paraffin charge. Air is introduced to each reactor in the amount of 1.3 SCF per hour per pound of parraffin present in to the first reactor and at the rate of 0.7 SCF/hr./lb. in the second reactor. The reactors are operated at 10 p.s.i.g. and are each equipped with means to separate overhead by-product water. The average residence time of the paraffin in the first reactor is 3.1 hours and in the second reactor 2.6 hours, thereby providing a total conversion of paraffin to 17.1 weight percent borate esters, about 0.55 weight percent oxygenates, and about 0.1 weight percent olefins, with the remainder of the organic material being unconverted paraffin. The reactor effluent stream is first fractionated by vacuum stripping at 365° F. and 5 mm pressure to obtain a bottom stream of stripped borate esters and an overhead containing predominantly $C_{10}$ to $C_{14}$ unreacted n-paraffin, 0.2 weight percet secondary alcohols, 0.1 weight percent olefins, 0.12 weight percent acids, 0.24 weight percent ketones and 0.54 weight percent borate esters. The bottom stream of stripped borate esters, other polyoxygenated by-products and traces of unreacted n-paraffin are contacted with water at 180° F. in an in-line mixer at a weight ratio of water to borate ester containing stream of 2:1 and a top organic layer is separated from a bottom layer composed of aqueous boric acid.

The top organic layer composed of 85 weight percent secondary alcohols, 0.6 weight percent unreacted paraffins, 1.2 weight percent boric acid and the remainder polyoxygenated paraffins is fractionated at 390° F. and 2 mm pressure to remove overhead 101 pounds of secondary alcohols of approximately 99 percent purity. The bottoms comprising $C_{10}$ to $C_{14}$ polyoxygenated paraffins are steam stripped to form an overhead composed of 30 weight percent acids, 12 weight percent ketones, 38 weight percent glycols, 17 weight percent esters and 3 weight percent boric acid. This overhead is combined with the first fractionated overhead containing predominantly $C_{10}$ to $C_{14}$ unreacted paraffin to form a recycle stream comprising 0.1 weight percent olefin, 0.5 weight percent acids, 0.4 weight percent ketones, 0.5 weight percent glycols, 0.7 weight percent borate esters, 0.4 weight percent boric acid and the remainder unreacted paraffin.

The recycle stream is introduced into an initial hydrogenation reactor at the rate of about 722 pounds per hour and hydrogenated at 400° F. with 25 pounds per hour of hydrogen at 800 p.s.i.g. at a liquid hourly space velocity of 2.5 in the presence of a cobalt-molybdenum on alumina catalyst. The product of the initial hydrogenation zone is introduced into a subsequent hydrogenation reactor at the rate of 719 pounds per hour and hydrogenated at 670° F. with 25 pounds per hour of hydrogen at 800 p.s.i.g. at a liquid hourly space velocity of 2.0 in the presence of a 0.75 weight percent platinum, 0.4 weight percent potassium oxide on gamma alumina catalyst. After separating hydrogen and water, the hydrogenated product is essentially free of oxygenated by-products, the n-paraffin content is in excess of 99 weight percent and the product is recycled for introduction to the stirred tank reactors. Virtually no methane, light hydrocarbons and isoparaffins are produced during hydrogenation. For 101 pounds of 99 percent purity secondary alcohol, there is required 103 pounds of fresh n-paraffin feed in the continuous process.

EXAMPLE IV

A recycle stream similar to that in Example III is hydrogenated at 550° F. and 800 p.s.i.g. with 3.5 pounds of hydrogen per 100 pounds of recycle feed over a nickel on kieselguhr hydrogenation catalyst at a liquid hourly space velocity of 2.0. About 12 weight percent of the feed is converted to paraffins lighter than $C_6$. For 101 pounds of 99 percent purity secondary alcohol, there is required 115 pounds of fresh n-paraffin feed in the continuous process employing the catalytic hydrogenation described in this example. It will be seen that the claimed invention employing the catalyst illustrated in Example III is more selective in converting the mixture to n-paraffin than the conventional hydrogenation catalyst employed in Example IV.

EXAMPLE V

Example III is repeated except that the recycle stream is first introduced through a bed of alumina at 400° F. acting as a guard chamber and thereafter catalytic hydrogenation of the recycle stream is undertaken at 670° F. in the presence of a 3.0 weight percent nickel oxide - 12.0 weight percent molybdenum oxide — 0.2 weight percent lithium oxide on eta alumina catalyst. The results of hydrogenation and the composition of the hydrogenated product are similar to Example III.

We claim:

1. In a process for selectively converting a mixture of n-paraffin and oxygenated n-paraffin by-products, said n-paraffin and by-products having from 6 to 30 carbon atoms, to a substantially pure n-paraffin recycle feedstock by catalytically hydrogenating said mixture and converting said oxygenated n-paraffin by-products to the corresponding n-paraffin, the improvement which comprises catalytically hydrogenating said mixture in the absence of substantial isomerization and hydrocracking at a temperature of from about 600° to 750° F. in the presence of a catalyst composed of alumina, from about 0.1 to 5.0 weight percent of a Group VIII metal and from about 0.05 to 2.0 weight percent of an alkali metal oxide or alkaline earth metal oxide or thallous oxide or mixtures thereof impregnated on said alumina to convert said by-products to n-paraffins.

2. A process according to claim 1 wherein said Group VIII metal is platinum, palladium, rhodium, ruthenium, nickel or cobalt.

3. A process according to claim 1 wherein said alkali metal oxide is lithium oxide, sodium oxide, potassium oxide, rubidium oxide or cesium oxide.

4. A process according to claim 1 wherein said alkaline earth metal oxide is calcium oxide, strontium oxide or barium oxide.

5. A process according to claim 1 wherein said catalyst contains thallous oxide.

6. A process according to claim 1 wherein said catalyst additionally contains a Group VIB metal oxide.

7. A process according to claim 6 wherein said Group VIB metal oxide is molybdenum oxide.

8. A process according to claim 6 wherein said Group VIB metal oxide is tungsten oxide.

9. A process according to claim 1 wherein said catalyst additionally contains a Group VIIB metal.

10. A process according to claim 9 wherein said Group VIIB metal is rhenium.

11. A process according to claim 1 wherein said Group VIII metal is platinum.

12. A process according to claim 1 wherein said Group VIII metal is rhodium.

13. A process according to claim 1 wherein said catalyst comprises platinum, lithium oxide and alumina.

14. A process according to claim 1 wherein said catalyst comprises platinum, thallous oxide and alumina.

15. A process according to claim 1 wherein said catalyst comprises platinum, potassium oxide and alumina.

16. A process according to claim 1 wherein said catalyst comprises nickel oxide, molybdenum oxide, barium oxide and alumina.

17. A process according to claim 1 wherein said catalyst comprises nickel oxide, molybdenum oxide, lithium oxide and alumina.

18. A process according to claim 1 wherein said temperature is from 610° to 700° F.

19. A process according to claim 1 wherein said mixture is initially catalytically hydrogenated at from about 350° to 500° F.

20. A process according to claim 19 wherein said mixture is initially catalytically hydrogenated at from about 400° to 450° F.

21. A process according to claim 1 wherein said mixture is additionally and subsequently catalytically hydrogenated at from about 450° to 650° F.

* * * * *